US00PP18540P2

(12) United States Plant Patent
Spencer

(10) Patent No.: US PP18,540 P2
(45) Date of Patent: Mar. 4, 2008

(54) *PHYGELIUS* PLANT NAMED 'CROPURPRI'

(50) Latin Name: *Phygelius aequalis*
Varietal Denomination: Cropurpri

(76) Inventor: Malcolm Spencer, Croftway Hall, Yapton Road, Barnham, Bognor Regis, West Sussex (GB), PO22 OBQ ( * ) Notice: Subject to any disclaimer, the term of this patent is extended or adjusted under 35 U.S.C. 154(b) by 30 days.

(21) Appl. No.: 11/493,957

(22) Filed: Jul. 26, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Louanne Krawczewicz Myers

(57) ABSTRACT

A new cultivar of *Phygelius* named 'CROPURPRI' that is characterized by compact upright habit, purple stems, purple flowers, and dark-green foliage. In combination these traits set 'CROPURPRI' apart from all other existing varieties of *Phygelius* known to the inventor.

2 Drawing Sheets

Genus: *Phygelius*. Species: *aequalis*.
Denomination 'CROPURPRI'.

BACKGROUND OF THE INVENTION

The present invention relates to a new and distinct cultivar of *Phygelius,* commonly known as Cape Fuchsia which was bred by the inventor at the inventor's nursery in West Sussex, United Kingdom. The new cultivar is known botanically as *Phygelius aequalis* and is referred to hereinafter by the cultivar name 'CROPURPRI'. 'CROPURPRI' is one of four co-pending applications by the inventor relating to new cultivars of *Phygelius.* The other three co-pending applications are titled 'CROSNOQUE' (U.S. patent application Ser. No. 11/494,374), 'CROCORPRI' (U.S. patent application Ser. No. 11/494,379) and 'CROYELSOV' (U.S. patent application Ser. No. 11/494,350). Taken together, these four cultivars constitute the Croftway Series of *Phygelius* and individual plants are grown as annual container plants in most regions of the United States or as perennial plants in regions in U.S.D.A. hardiness zones of 8 or higher.

The new *Phygelius* variety named 'CROPURPRI' is a hybrid plant that resulted from a formal breeding program developed by the inventor in 1997. The breeding program was developed with the goal of producing new varieties of *Phygelius* that exhibit new flower color. In August 1999 the inventor chose the parents as breeding candidates. The inventor conducted controlled cross-pollination using an unnamed, (unpatented) seedling of *Phygelius aequalis* as the female parent, and a *Phygelius aequalis* 'Yellow Trumpet' (unpatented) as the male parent. Cross-pollination was conducted at the inventor's nursery in West Sussex, United Kingdom in 1999. The seed was collected and sown by the inventor the following February 2000. First flowering occurred, and initial assessment was made in July 2000. Back-crosses were carried out in September, from which new seed was collected and sown in February 2001. The first-flowering and final assessment, were made by the inventor in September 2001.

'CROPURPRI' was selected by the inventor at his nursery in West Sussex, United Kingdom in 2001. Selection was based on the criteria of new flower color, habit, and quantity of flowers. 'CROPURPRI' is distinguishable from the female parent by flower color, greater number of flowers per stem, and pronounced compact upright habit. The female parent exhibits deep-pink flowers, whereas 'CROPURPRI' exhibits flowers that are purple in color. 'CROPURPRI' is distinguishable from the male parent by flower color, greater number of flowers per stem, and pronounced compact upright habit. No comparison varieties, with similar flower color, are known to the inventor, 'CROPURPRI' is unique and distinguishable from all other varieties of *Phygelius* by new flower color, quantity of flowers, and pronounced compact habit.

The new *Phygelius* variety named 'CROPURPRI' is free flowering and exhibits compact upright habit, purple flowers, purple stems, and dark-green foliage. The plant dimensions at maturity are 75 cm. in height and 45 cm. in width. 'CROPURPRI' blooms late summer and fall, and is hardy to USDA Zone 8. Cultural conditions include open well-draining soil with good humus content, full sun, and moderate to regular water.

'CROPURPRI' was first asexually propagated by the inventor, in 2001 in West Sussex, United Kingdom. The method of asexual propagation used was softwood cuttings. Since that time, under careful observation, the distinguishing characteristics have been determined stable, uniform, and reproduce true to type in successive generations of asexual propagation.

SUMMARY OF THE INVENTION

The following represent the distinguishing characteristics of the new *Phygelius* cultivar named 'CROPURPRI'. In combination these traits set 'CROPURPRI' apart from all other existing varieties of *Phygelius* known to the inventor. 'CROPURPRI' has not been tested under all possible conditions and phenotypic differences may be observed with variations in environmental, climatic, and cultural conditions, however, without any variance in genotype.

1. 'CROPURPRI' exhibits compact upright habit.
2. 'CROPURPRI' exhibits purple flowers late summer and fall.
3. 'CROPURPRI' is free flowering.
4. 'CROPURPRI' exhibits dark-green foliage.
5. 'CROPURPRI' exhibits purple stems.
6. 'CROPURPRI' reaches 75 cm. in height and 45 cm. in width at maturity.
7. Cultural conditions of 'CROPURPRI' include full sun, open well-draining soil with good humus content, and moderate to regular water.
8 . 'CROPURPRI' is hardy to USDA Zone 8.

BRIEF DESCRIPTION OF THE DRAWINGS

The accompanying color drawings illustrate the overall appearance of the new *Phygelius* cultivar named 'CROPURPRI' showing the color as true as it is reasonably possible to obtain in color reproductions of this type. Color in the drawings may differ from the color values cited in the detailed botanical description, which accurately describes the actual color of the new variety 'CROPURPRI'.

The drawing labeled

The drawing labeled

Figure 1:
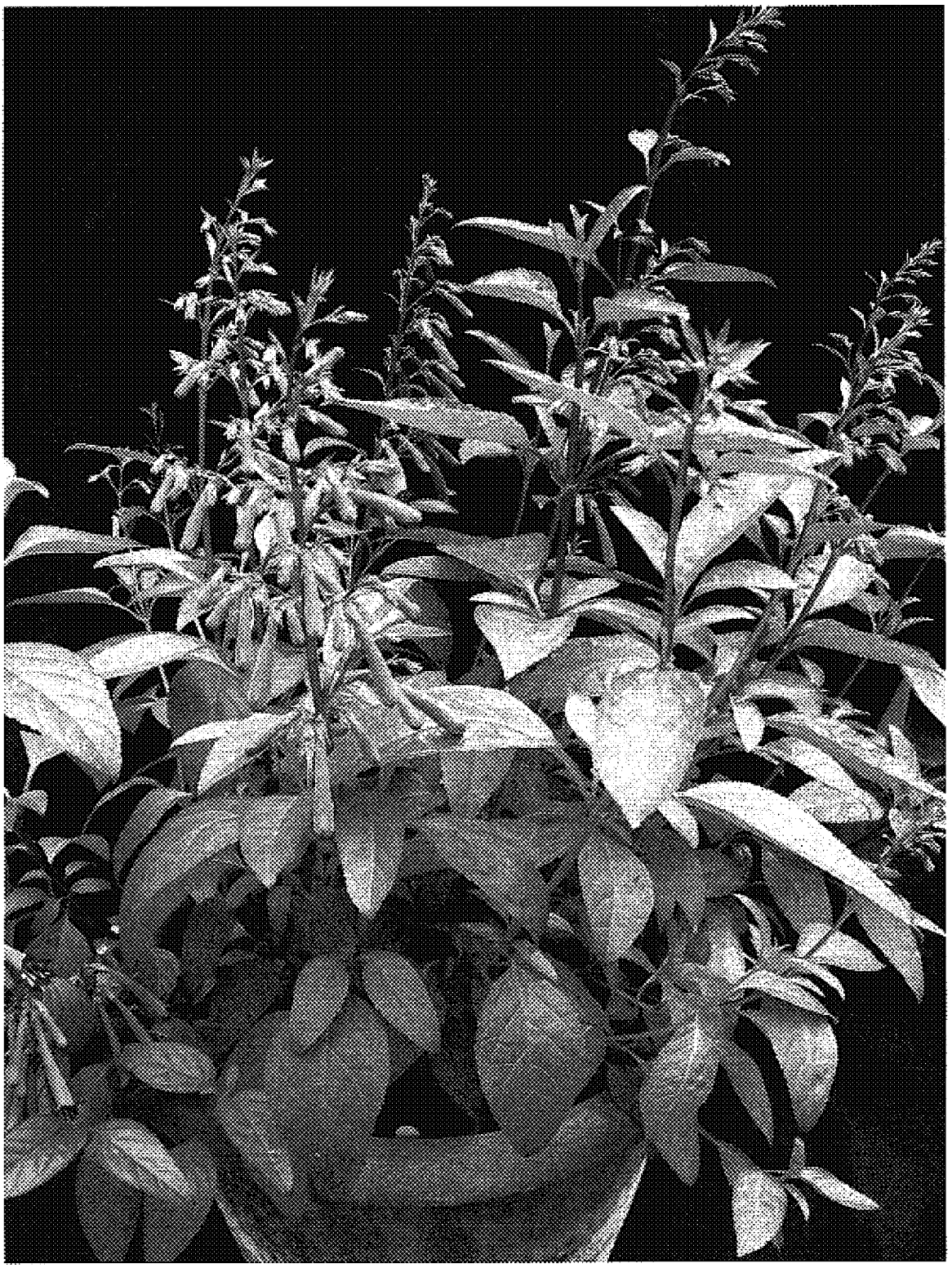
FIG. 1 depicts a side view of the plant illustrating habit.
Figure 2:
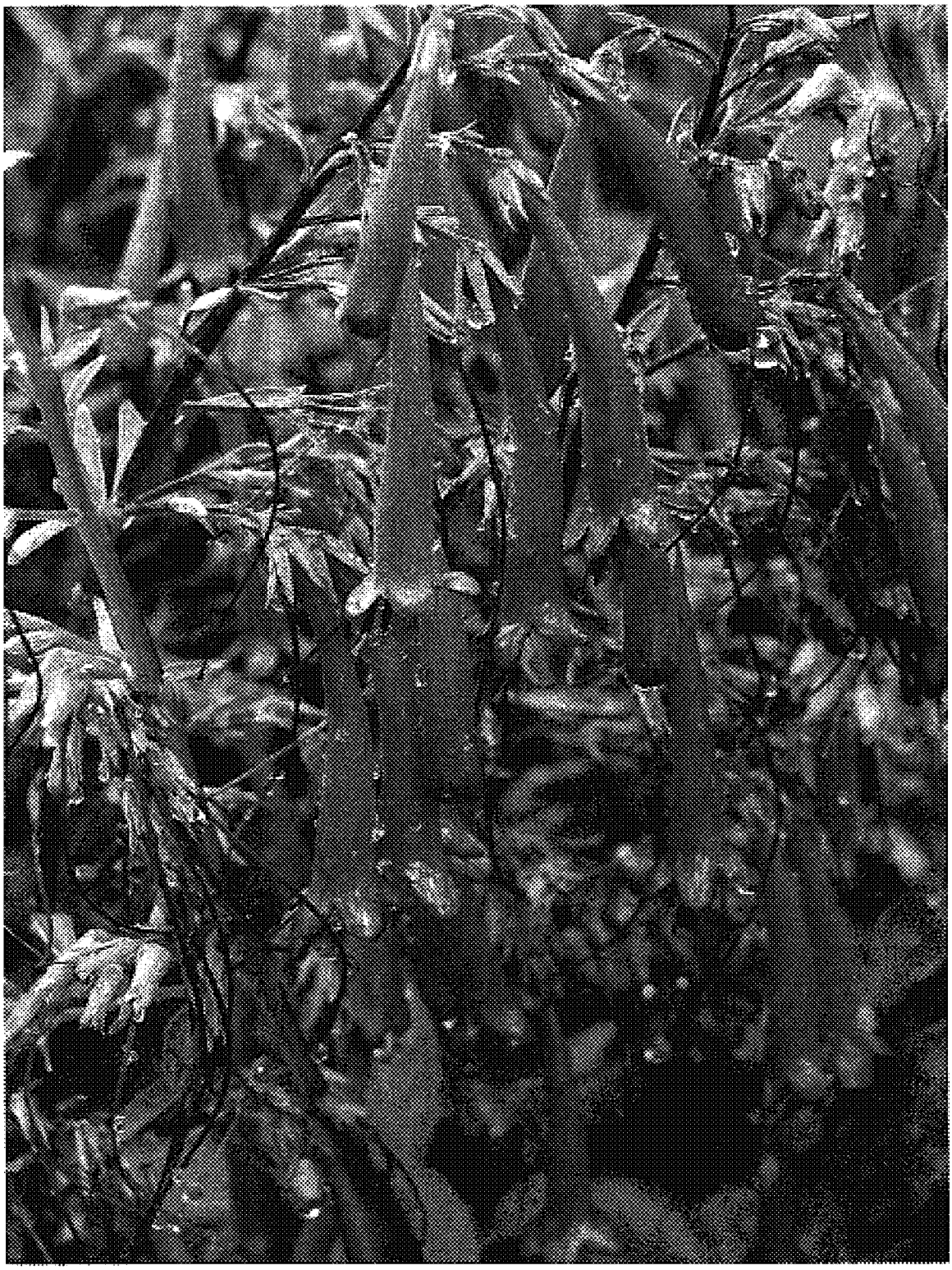
FIG. 2 depicts a close-up view of the flower.

All photographs were taken using conventional techniques and although color may appear different from actual color due to light reflectance, they are as accurate as possible by conventional photography.

BOTANICAL DESCRIPTION OF THE PLANT

The following is a detailed botanical description of the *Phygelius* cultivar named 'CROPURPRI'. Data was collected in Arroyo Grande, Calif. from 4 month old plants grown out-of-doors in 1-liter containers. Color determinations are in accordance with the 2001 Royal Horticultural Society Colour Chart of London, England except where general color terms of ordinary dictionary significance are used. The growing requirements are similar to the species.

Botanical classification: *Phygelius aequalis* 'CROPURPRI'.
Family: Schrophulariaceae.
Genus: *Phygelius.*
Species: *aequalis.*
Denomination: 'CROPURPRI'.
Common name: Cape fuchsia.
Plant use: Ornamental for use in the landscape.
Parentage: *Phygelius aequalis* 'CROPURPRI' is a hybrid plant seedling resulting from controlled cross-pollination of the following parents:
- *Female parent.*—An unnamed, unpatented seedling of *Phygelius aequalis.*
- *Male parent.*—A *Phygelius aequalis* 'Yellow Trumpet' (unpatented).

Type: Shrub.
Vigor: Vigorous.
Habit: Dense compact.
Dimensions (at one year): 45 cm. in height and 30 cm. in width.
Dimensions (at maturity): 75 cm. in height and 45 cm. in width.
Hardiness: USDA Zone 8.
Asexual propagation: Softwood cuttings.
Root system: Fine and fibrous.
Cultural conditions: Full sun, open well-draining soil with good humus content, and moderate to regular water.
Time to initiate roots: 4–6 weeks.
Crop time: 4–8 months to produce a finished 1-liter container.
Disease susceptibility: Powdery mildew when grown under cover.
Pest susceptibility: Whitefly and greenfly.
Seasonal interest: Flowers late summer and fall.
Stem:
- *Average number of branches per plant.*—7 per 1-gallon plant.
- *Stem shape.*—Angular.
- *Internode length* (*average*).—4.50 cm.
- *Stem width.*—0.40 cm. in width.
- *Stem length.*—Ranges from 23–33 cm.
- *Stem surface.*—Glabrous.
- *Stem color.*—N79A.

Foliage:
- *Foliage type.*—Evergreen.
- *Leaf arrangement.*—Opposite.
- *Average number of leaves per plant.*—88 per 1-gallon plant.
- *Leaf division.*—Simple.
- *Leaf shape.*—Lanceolate.
- *Leaf base.*—Rounded.
- *Leaf apex.*—Acute.
- *Leaf venation.*—Pinnate.
- *Vein color* (*adaxial and abaxial surfaces*).—139C.
- *Leaf attachment.*—Petiolate.
- *Petiole dimensions.*—2 cm. in length and 2.50 mm. in width.
- *Petiole shape.*—Sulcate.
- *Petiole color.*—N79A.
- *Petiole surface.*—Glabrous.
- *Leaf margin.*—Crenate.
- *Leaf dimensions* (*average*).—6.50 cm. in length and 3 cm. in width.
- *Leaf color* (*adaxial surface*).—139A.
- *Leaf color* (*abaxial surface*).—N138C.
- *Leaf surfaces* (*adaxial and abaxial*).—Glabrous.
- *Leaf appearance* (*adaxial surface*).—Semi-glossy.
- *Leaf appearance* (*abaxial surface*).—Matte.
- *Stipules.*—Present.
- *Stipule color.*—139A.
- *Stipule apex.*—Acute.
- *Stipule base.*—Attenuate.
- *Stipule margins.*—Crenate.
- *Stipule dimensions.*—6 mm. in length and 6 mm. in width.
- *Foliar fragrance.*—None observed.

Flower:
- *Inflorescence.*—Raceme.
- *Inflorescence dimensions.*—10 cm. in length and 6 cm. in width.
- *Inflorescence form.*—One-sided.
- *Quantity of flowers.*—25–35 per inflorescence.
- *Quantity of flowers and buds per plant.*—Approximately 1200 at peak flower.
- *Form.*—Solitary.
- *Persistent or self-cleaning.*—Self-cleaning.
- *Aspect.*—Pendulous.
- *Peduncle strength.*—Strong, flowers do not detach in wind.

*Peduncle dimensions.*—2 cm. in length and 2 mm. in diameter.
*Peduncle shape.*—Cylindroid.
*Peduncle surface.*—Glabrous.
*Peduncle color.*—N79A.
*Pedicel dimensions.*—2.25 cm. in length and 1.50 mm. in width.
*Pedicel shape.*—Cylindroid.
*Pedicel surface.*—Glabrous.
*Pedicel color.*—N79A.
*Bud shape.*—Claviform.
*Bud surface.*—Glabrous.
*Bud dimensions.*—2.50 cm. in length and 0.50 cm. in width.
*Bud apex.*—Truncate.
*Bud base.*—Rounded.
*Bud color.*—71B.
*Bud rate of opening.*—Approximately 5 days from tight bud to fully open and extended flower.
*Flower shape.*—Tubular with five lobes.
*Flower diameter* (*at apex*).—1.25 cm.
*Flower diameter* (*at base*).—0.25 cm.
*Flower depth* (*tube and lobes*).—4.50 cm.
*Flower aspect.*—Pendulous.
*Lastingness of a single flower on the plant.*—1 week average.
*Corolla tube diameter.*—0.60 cm.
*Corolla tube surface.*—Glabrous.
*Corolla tube color* (*dorsal surface*).—71C.
*Corolla tube color* (*ventral surface*).—162D.
*Petals.*—5 in number.
*Fused or unfused.*—Petals are fused, except upper 15% of petals are free.
*Petal shape.*—Upper (free) part of petal is broad ovate.
*Petal length.*—Overall length is 3.8 cm., length unfused part is 0.40 cm.
*Petal width, unfused part.*—3 mm.
*Petal color* (*ventral surface*).—Individual colors 71A and N79A and 162D.
*Petal color* (*dorsal surface*).—71C.
*Petal margin.*—Entire.
*Petal apex.*—Subacute.
*Petal surface* (*abaxial*).—Glabrous.
*Petal surface* (*adaxial*).—Stipitate glandular.
*Calyx shape.*—Campanulate.
*Calyx dimensions.*—0.50 cm. in diameter and 1 cm. in length.
*Calyx surface.*—Glabrous.
*Calyx color.*—N79B.
*Sepals.*—Five in number.
*Sepal margin.*—Entire.
*Sepal surface.*—Glabrous.
*Sepal arrangement.*—Campanulate.
*Sepal dimensions.*—9 mm. in length and 3 mm. in width.
*Fused or unfused.*—Sepals are overlapping.
*Sepal apex.*—Acute.
*Sepal base.*—Fused, lower 20% (basal 20%).
*Sepal color, adaxial surface.*—187C.
*Sepal color, abaxial surface.*—187B.
*Blooming period.*—Late summer and fall.
*Fragrance.*—None observed.

Reproduction organs:
*Stamens.*—4 in number.
*Stamen attachment.*—Filament adnate to corolla tube.
*Stamen color.*—71A.
*Stamen length.*—4.75 cm.
*Anther shape.*—Rotund.
*Anther dimensions.*—2 mm. in width and 3 mm. in length.
*Anther color.*—197A.
*Pollen color.*—197A.
*Pollen quantity.*—Moderate.
*Pistil.*—One.
*Pistil color.*—71A.
*Pistil length.*—5 cm.
*Stigma.*—Penicillate.
*Stigma color.*—71A.
*Ovary position.*—Superior.
*Ovary color.*—N144C.
*Ovary dimensions.*—0.60 cm. in height and 0.40 cm. in width.
*Ovary shape.*—Ovoid.

Seed: None observed to date.

It is claimed:

1. A new and distinct variety of *Phygelius* plant named 'CROPURPRI' as described and illustrated.

* * * * *